United States Patent
Lin (10) Patent No.: US 11,993,798 B2
(45) Date of Patent: May 28, 2024

(54) METHOD FOR MANUFACTURING BACTERIALLY INDUCED CRYSTAL PARTICLE

(71) Applicant: ACON-HOLDING INC., New Taipei (TW)

(72) Inventor: Pao-Hung Lin, New Taipei (TW)

(73) Assignee: ACON-HOLDING INC., New Taipei (TW)

( * ) Notice: Subject to any disclaimer, the term of this patent is extended or adjusted under 35 U.S.C. 154(b) by 42 days.

(21) Appl. No.: 17/743,469

(22) Filed: May 13, 2022

(65) Prior Publication Data

US 2022/0275404 A1    Sep. 1, 2022

Related U.S. Application Data

(62) Division of application No. 15/816,156, filed on Nov. 17, 2017, now Pat. No. 11,359,215.

(30) Foreign Application Priority Data

Nov. 30, 2016 (TW) .................................. 105139567

(51) Int. Cl.
| | | |
|---|---|---|
| C12P 1/04 | (2006.01) | |
| C01B 19/00 | (2006.01) | |
| C01G 1/02 | (2006.01) | |
| C01G 1/12 | (2006.01) | |
| C01G 41/00 | (2006.01) | |
| C01G 41/02 | (2006.01) | |
| C09K 5/14 | (2006.01) | |
| C12P 3/00 | (2006.01) | |
| B82Y 5/00 | (2011.01) | |
| C12N 1/00 | (2006.01) | |
| C12R 1/00 | (2006.01) | |

(52) U.S. Cl.
CPC .............. *C12P 1/04* (2013.01); *C01B 19/007* (2013.01); *C01G 1/02* (2013.01); *C01G 1/12* (2013.01); *C01G 41/00* (2013.01); *C01G 41/02* (2013.01); *C09K 5/14* (2013.01); *C12P 3/00* (2013.01); *B82Y 5/00* (2013.01); *C01P 2002/82* (2013.01); *C01P 2004/03* (2013.01); *C01P 2004/34* (2013.01); *C12N 1/00* (2013.01); *C12R 2001/00* (2021.05)

(58) Field of Classification Search
None
See application file for complete search history.

(56) References Cited

U.S. PATENT DOCUMENTS

| | | | |
|---|---|---|---|
| 8,685,550 B2 * | 4/2014 | Kim ...................... | H01M 4/621 428/34.1 |
| 2014/0087439 A1 * | 3/2014 | Otsubo .................... | C12P 9/00 210/601 |

FOREIGN PATENT DOCUMENTS

WO    WO 2011/141418    * 11/2011

* cited by examiner

*Primary Examiner* — Vera Afremova
(74) *Attorney, Agent, or Firm* — Chieh-Mei Wang (57) ABSTRACT

A method for manufacturing bacterially induced crystal particle includes culturing bacteria in a culture medium including a carbon source and a raw metal material including a transition metal, so that the bacteria induce a raw metal material to undergo a reduction-oxidation reaction; isolating a wet powder material from the culture medium; and drying the wet powder material to obtain a powder material. The powder material includes at least one bacterially induced crystal particle.

20 Claims, 6 Drawing Sheets

METHOD FOR MANUFACTURING BACTERIALLY INDUCED CRYSTAL PARTICLE

CROSS-REFERENCE TO RELATED APPLICATION

This non-provisional application is a divisional of U.S. patent application Ser. No. 15/816,156, filed on Nov. 17, 2017, which claims priority under 35 U.S.C. § 119(a) to Patent Application No. 105139567 in Taiwan, R.O.C., filed on Nov. 30, 2016, the entire contents of which are hereby incorporated by reference.

FIELD OF THE INVENTION

The instant disclosure relates to preparation techniques of nanomaterial, and more particular to a bacterially induced crystal particle, a thermal conductive material, and a method for manufacturing bacterially induced crystal particle.

BACKGROUND

Organisms like microorganisms, plants, and animals can become minerals in nature. A phenomenon called biomineralization means forming inorganic minerals in organisms. Cells of the organism are participated into the process of biomineralization, so that inorganic elements in the environments are selectively deposited on certain organic substances to form minerals. The microbial mineralization can be divided into two mineralization mechanisms, i.e., biologically induced mineralization (BIM) and biologically controlled mineralization (BCM).

The biologically induced mineralization of microorganisms can be further divided into two types, passive or active. The biologically induced mineralization in passive type is related to surface nucleation growth of the minerals resulted from nonspecific bonding between cations and anions in the nature. Regarding the biologically induced mineralization in active type, the metal ions combined on the surface of the microorganism may directly undergo a reduction-oxidative reaction and be transferred into minerals, or the side products in the metabolism of cells may react with ions in the environment to form minerals on the cell surface.

The minerals are deposited on an organic matrix of a cell or on the surface or the interior of a vesicle of the cell. Accordingly, the organisms can control or confine the nucleation, growth, composition, size, and the position in the cell, of the mineral in some extent. This process is called biologically controlled mineralization. The mineral grains formed by biologically controlled mineralization usually have uniform structure, narrow size distribution, and specific and uniform types, uniform crystal habits, etc. In addition, during the biologically induced mineralization, the formation of the minerals can be induced when the ambient environment satisfies certain conditions. Conversely, during the biologically induced mineralization, all the environmental conditions in the cell (e.g., pH value, reduction-oxidation potential (Eh)) are controlled by the cell, therefore, the formation of the minerals can be hardly achieved.

SUMMARY OF THE INVENTION

In view of this, a bacterially induced crystal particle a thermal conductive material, and a method for manufacturing bacterially induced crystal particle are provided.

In some embodiments, a bacterially induced crystal particle is formed by a composite shell. The composite shell encloses a hollow space. The composite shell includes a biomaterial and a metallic material. Wherein, the biomaterial includes a cell wall or a cell membrane of bacteria. The metallic material includes oxides, sulfides, selenides, acid salt compounds of a transition metal or any combination thereof. The bacterially induced crystal particle is spheric or rod-shaped. When the bacterially induced crystal particle is spheric, the composite shell is formed by two dome-shaped portions, and a thickness of each of the dome-shaped portions is not less than $\frac{1}{73}$ of a diameter of the bacterially induced crystal particle, when the bacterially induced crystal particle is rod-shaped, the composite shell is formed by a cylindrical portion and the two dome-shaped portions connected to two ends of the cylindrical portion, the thickness of each of the dome-shaped portions is not less than $\frac{1}{73}$ of a width of the bacterially induced crystal particle, and a thickness of the cylindrical portion is not less than $\frac{1}{37}$ of the width of the bacterially induced crystal particle.

In some embodiments, a method for manufacturing bacterially induced crystal particle may include culturing bacteria in a culture medium, so that the bacteria induce a raw metal material to undergo at reduction-oxidation reaction; isolating a wet powder material from the culture medium; and drying the wet powder material to obtain a powder material. Wherein, the culture medium may include a carbon source and a raw metal material, and the raw metal material includes a transition metal. The powder material may include the aforementioned bacterially induced crystal particle.

In one embodiment, a thermal conductive material may comprise the aforementioned bacterially induced crystal particle.

As above, the bacterially induced crystal particle, the thermal conductive material, and the method for manufacturing bacterially induced crystal particle, in accordance with one of the embodiments of the instant disclosure, are suitable for manufacturing a novel material, so that the material has a great low thermal conductivity. In addition, the method for manufacturing the bacterially induced crystal particle in accordance with one of the embodiments of the instant disclosure is easy, low cost, and can be directly applied in mass production.

BRIEF DESCRIPTION OF THE DRAWINGS

The instant disclosure will become more fully understood from the detailed description given herein below for illustration only, and thus not limitative of the instant disclosure, wherein.

DETAILED DESCRIPTION

Hereinafter, the terminology "weight percentage" means the weight percentage calculated by taking the number of moles of the carbon in the carbon source as a standard.

Figure 1:
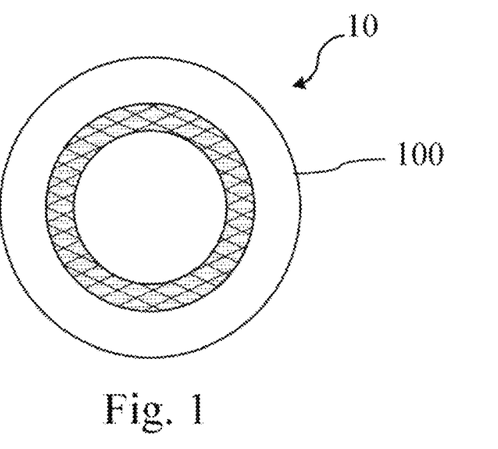
FIG. 1 illustrates a schematic sectional vies of a bacterially induced crystal particle of one embodiment of the instant disclosure.

Please refer to FIG. 1. In some embodiments, the bacterially induced crystal particle 10 may comprise a composite shell 100. The interior of the composite shell 100 is hollow, and the composite shell 100 comprises a biomaterial and a metallic material. The biomaterial comprises a cell wall or a cell membrane of bacteria. For example, the organic substance may only include cell wall or cell membrane of bacteria as well as a small amount of other carbon-containing organics. The weight percentage of the bio material may be in a range of 5 to 80% over the composite shell, and the weight percentage of the biomaterial over the composite shell is greater than the weight percentage of the metallic material over the composite shell. The metallic material may be oxides, sulfides, selenides, acid salt compounds of a transition metal, or any combination thereof. In some embodiments, the metallic material may be oxides, sulfides, or selenides of the transition metal. In addition, the weight percentage of the transition metal element of the metallic material may be in the range from 3 to 75% over the composite shell. In some embodiments, bacteria are the template in the formation of the composite shell with transition-metal oxide mineral, transition-metal sulfide mineral, transition-metal selenide mineral, transition-metal acid salt mineral, other alternative transition metal compounds, or any combination thereof.

In some embodiments, the biomaterial may be organic substances comprising cell wall or cell membrane of Gram-negative bacteria. For example, the biomaterial may be organic substances, and the organic substances are cell wall or cell membrane of *Shewanella* sp., *Pantoea* sp., *Pseudomonas aeruginosa*, or *Bacillus subtilis*; embodiments are not limited thereto. In some embodiments, the metallic material may be oxides, sulfides, selenides, or acid salt compounds of a transition metal, and the transition metal may be vanadium, niobium, tungsten, molybdenum, cobalt, zirconium, other alternative transition metal compounds, or any combination thereof. The metallic material excludes from copper compounds and zinc compounds. For example, the metallic material may be a salt compound of vanadic acid, niobic acid, tungstic acid, or molybdenic acid.

In some embodiments, the biomaterial and the metallic material may be collocated properly according to application requirements and material property consideration. For example, in the case where the biomaterial includes cell wall or cell membrane of *Shewanella* sp., the metallic material may be salt compounds of tungstic acid or molybdenic acid. In the case where the biomaterial includes cell wall or cell membrane of *Pantoea* sp., the metallic material may be formed by salt compounds of molybdenic acid, tungstic acid, or vanadic acid.

In some embodiments, the interior of the composite shell 100 is hollow, and the composite shell 100 has a certain thickness. The "thickness" means a distance between any point on the inner surface of the composite shell 100 and any point on the outer surface of the composite shell 100 having a minimal value. In some embodiments, the thickness of the composite shell 100 may be in a range of 5 to 50 nm. In some embodiments, the thickness of the composite shell 100 may be in a range of 20 to 40 nm. Furthermore, the composite shell 100 may be formed by two half portions, and the two half portions are dome-shaped.

Figure 2:
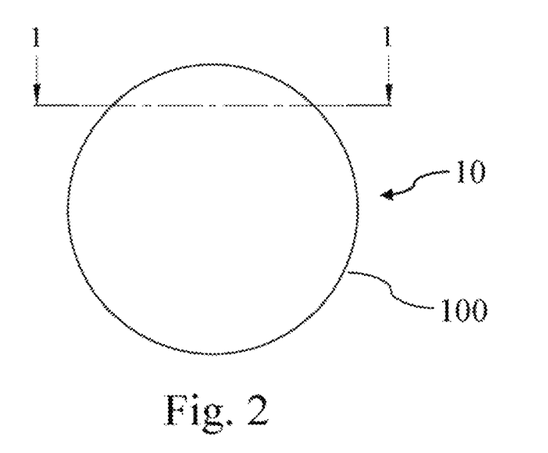
FIG. 2 illustrates a perspective view of the bacterially induced crystal particle of one embodiment of the instant disclosure.

Please refer to FIGS. 1 and 2, wherein FIG. 1 is a sectional view of the 1-1 line in FIG. 2. In some embodiments, the bacterially induced particle 10 may be spheric. The bacterially induced particle 10 has a diameter. The "diameter" means the diameter of a concentric sphere between the inner surface and the outer surface of the spheric composite shell 100. In addition, a minimal distance between any point on the inner surface of the composite shell 100 and any point on the surface of the concentric sphere is substantially the same as a minimal distance between any point on the outer surface of the composite shell 100 and any point on the surface of the concentric sphere. In some embodiments, the thickness of the two dome-shaped half portions is not less than 1/73 of the diameter of the bacterially induced particle 10. For example, the diameter of the bacterially induced particle 10 may be in a range of 0.2 to 2 μm. In some embodiments, the diameter of the bacterially induced particle 10 may be 1 μm.

Figure 3:
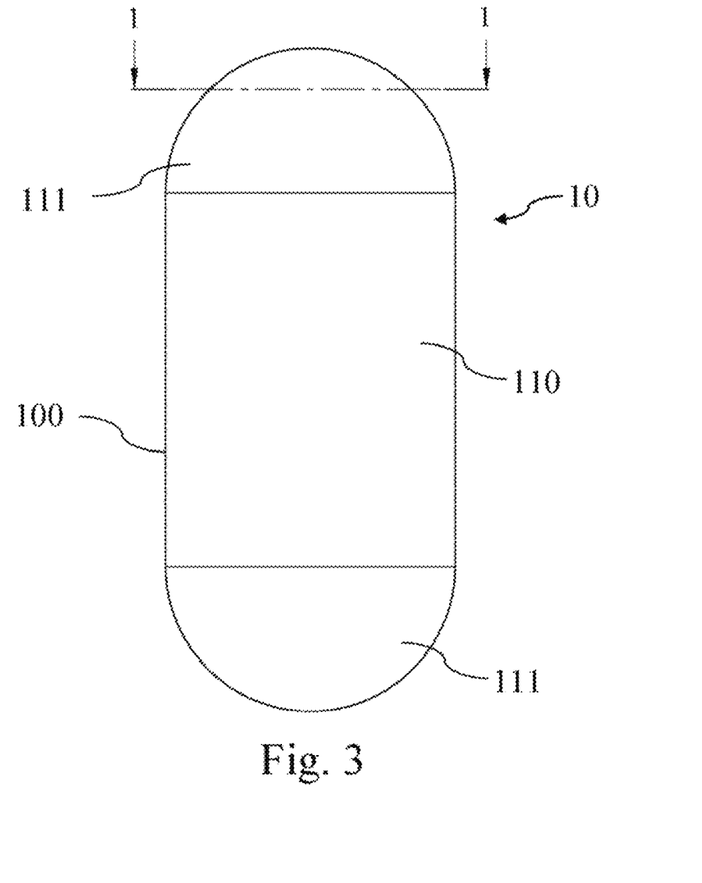
FIG. 3 illustrates a perspective view of the bacterially induced crystal particle of another embodiment of the instant disclosure.

Please refer to FIGS. 1 and 3 wherein FIG. 1 is a sectional view of the 1-1 line in FIG. 3. In some embodiments, the bacterially induced particle 10 may be rod-shaped and has certain width and length. The rod-shaped bacterially induced particle 10 may be formed by a cylindrical portion 110 and two dome-shaped portions 111 respectively connected to two ends of the cylindrical portion 110. Specifically, inner peripheries and outer peripheries of the two dome-shaped portions 111 are respectively connected to inner peripheries and outer peripheries of the two ends of the cylindrical portion 110. For each of the dome-shaped portions 111, regarding the sectional plane having a maximal area, the "width" means a maximal distance between any two points on a line connected by middle points, and the middle points is at the center of a minimal distance between any point on the inner periphery of the sectional plane and any point on the outer periphery of the sectional plane; namely, the "width" is the width of the cylindrical portion 110. For example, if the sectional plane of the maximal area of each of the dome-shaped portions 111 is a circle, the width is the diameter of a concentric circle between the inner periphery of the sectional plane and the outer periphery of the sectional plane. In addition, a minimal distance between any point on the inner periphery of the dome-shaped portion 111 and any point on the periphery of the concentric circle is substantially the same as that between any point on the outer periphery of the dome-shaped portion 111 and any point on the periphery of the concentric circle. In some embodiments, the thickness of each of the dome-shaped portions 111 is not less than 1/73 of the width of the bacterially induced particle 10, and the thickness of the cylindrical portion 110 is not less than 1/37 of the width of the bacterially induced particle 10. In some embodiments, the width of the rod-shaped bacterially induced particle 10 may be in a range of 0.2 to 2 μm. In some embodiments, the width of the rod-shaped bacterially induced particle 10 may be 1 μm. In addition, the "length" of the rod-shaped bacterially induced particle 10 means a maximal distance between a middle point of the top dome-shaped portion 111 and a middle point of the bottom dome-shaped portion 111, the middle point of the top dome-shaped portion 111 is at the center between a minimal distance between a top point of the outer surface of the top dome-shaped portion 111 and a top point of the inner surface of the top dome-shaped portion 111, and the middle point of the bottom dome-shaped portion 111 is at the center between a minimal distance between a top point of the outer surface of the bottom dome-shaped portion 111 and a top point of the inner surface of the bottom dome-shaped portion 111. In some embodiments, the length of the rod-shaped bacterially induced particle 10 may be in a range of 1 to 10 μm.

Figure 4:
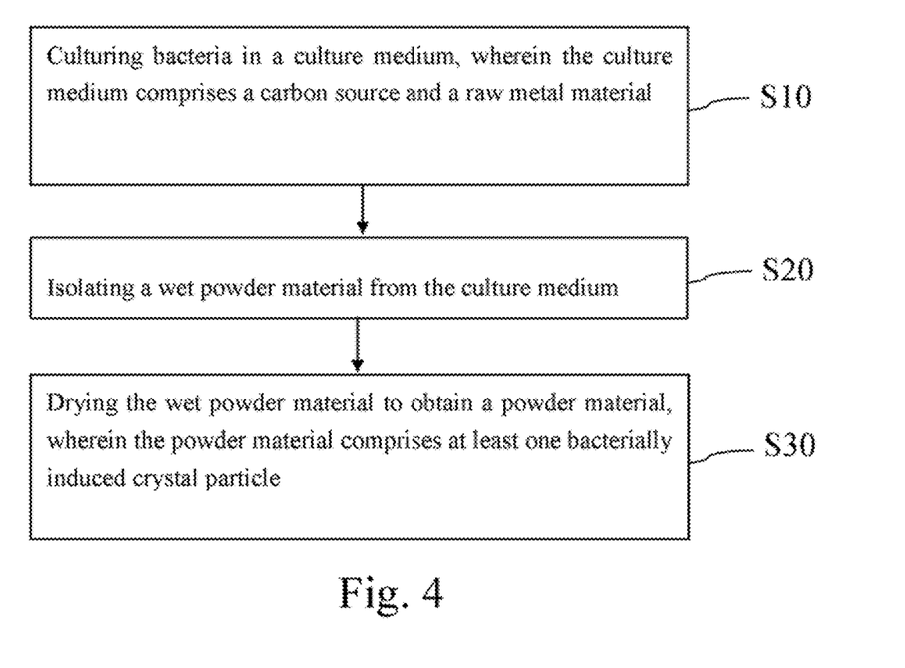
FIG. 4 illustrates a flowchart of a method for manufacturing bacterially induced crystal particle of one embodiment of the instant disclosure.

Please refer to FIG. 4. In some embodiments, the method for manufacturing bacterially induced crystal particle limy comprise following steps. Firstly, culturing bacteria in a culture medium (S10). Wherein, the culture medium may comprise a carbon source and a raw metal material. During the cultivation, the bacteria would induce the raw metal material to undergo a reduction-oxidation reaction. And then, isolating a wet powder material from the culture medium (S20). Last, drying the wet powder material to obtain a powder material (S30). The powder material may be in a dispersive powder form or in an aggregation bulk form. Wherein, the powder material may comprise the aforementioned bacterially induced crystal particle 10. Furthermore, in some embodiments of the step S20, bubbles are formed on an upper layer of the culture medium, and a suspension is isolated from the bubbles to obtain the wet powder material.

In some embodiments, the bacteria may be Gram-negative bacteria, e.g., *Shewanella* sp., *Pantoea* sp., *Pseudomonas aeruginosa, Bacillus subtilis*, other alternative Gram-negative bacteria, or any combination thereof. In one embodiment, the bacteria may be *Shewanella* sp., *Pantoea* sp., *Pseudomonas aeruginosa*, or *Bacillus subtilis*. The bacteria used in the culturing step is the source of the biomaterial of the composite shell of the bacterially induced crystal particle. In some embodiments, the raw metal material may be transition metal compounds, e.g., acid salt compounds of the transition metals or oxygen-contained compounds of the transition metals. For example, the raw metal material may be salt compounds of vanadic acid, niobic acid, tungstic acid, or molybdenic acid, salt compounds of other transition metals, or any combination thereof. The raw metal material excludes from copper compounds and zinc compounds. The raw metal material may be the source of the metallic material of the composite shell of the bacterially induced crystal particle. For example, the metallic material of the composite shell may be formed by the raw metal material itself or a product from a reduction-oxidation reaction of the raw metal material.

In some embodiments, proper bacteria and raw metal material may be selected to obtain a desired powder material according to production requirements. For example, the bacteria in the culture medium may be *Shewanella* sp., and the raw metal material may be salt compounds of tungstic acid or molybdenic acid. In another example, the bacteria in the culture medium may be *Pantoea* sp., and the raw metal material may be salt compounds of molybdenic acid, tungstic acid, or vanadic acid. Furthermore, in some embodiments, the concentration of the raw metal material and the concentration of the carbon source in the culture medium may be respectively in a range of 0.01 to 0.2 M (molar concentration). In one embodiment, the concentration of the raw metal material in the culture medium may be in a range of 0.1 to 0.2 M.

In some embodiments, the "carbon source" means any substance having carbohydrates as its major ingredient. The substance can provide energy for bacterial reproduction and growth, and the substance can be served as a source of essential carbon ingredients for bacterial synthesis. Any inorganic or organic carbon-containing compound capable of being utilized by microorganisms may be a carbon source, e.g., carbon dioxide, carbonates, saccharides or saccharide derivatives, alcohols, organic acids, lipids, hydrocarbons, aromatic compounds. For example, the carbon source may be glucose, sucrose, starch, fructose, lactose, lactates, formates, pyruvates, and/or amino acids. In some embodiments, the concentration of the carbon source in the culture medium may be in a range of 0.01 to 0.2 M. Furthermore, in some embodiments, the culture medium may be prepared by any proper commercial culture medium recipes, e.g., a Luria Broth (LB) medium, a M9 medium, other alternative culture medium, or any combination thereof.

Temperature has effect on bacterial growth. Therefore, the bacteria are cultured under a proper temperature which is suitable for the growth of the bacteria. In one embodiment of the step S10, the bacteria are cultured in the culture medium under an oxygen atmosphere at 37 degree Celsius. Culture time has effect on production of bacteria. If the culture time is too short, the production of bacteria would be insufficient, and the yield of the bacterially induced crystal particle would be poor. In one embodiment of the step S10, the bacteria are placed in the culture medium and cultured for at least three days. In another embodiment, the bacteria may be cultured for 3 to 5 days.

Figure 5:
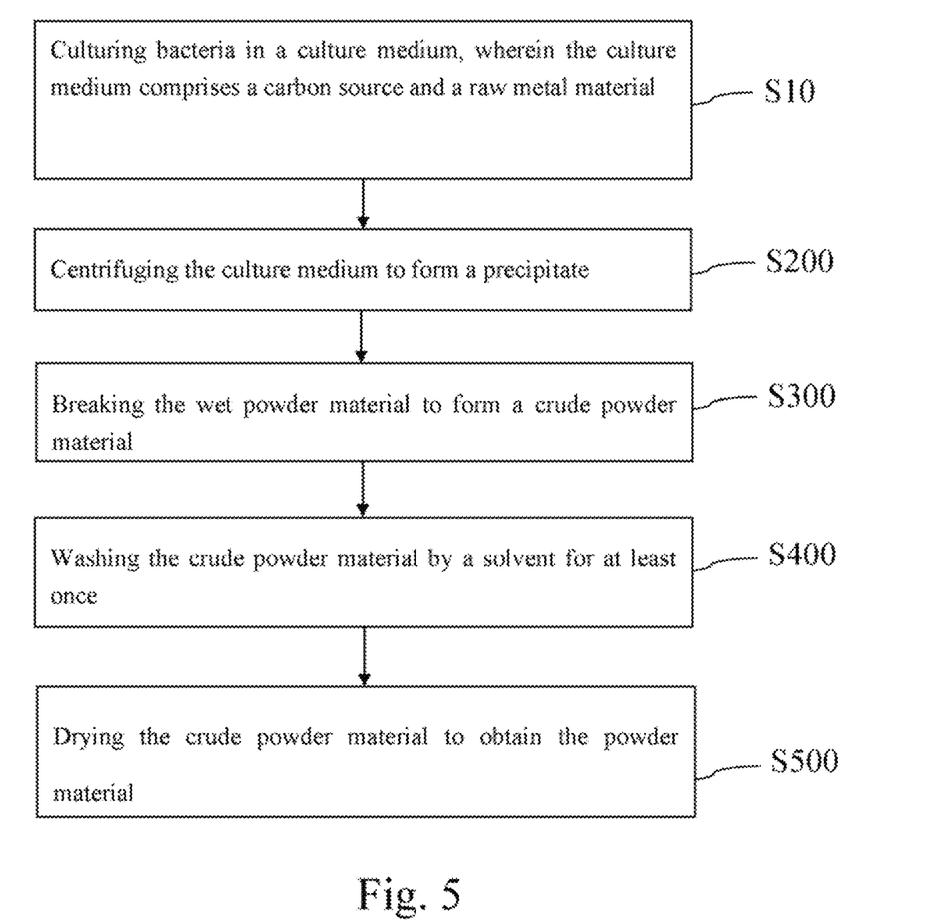
FIG. 5 illustrates a flowchart of the method for manufacturing bacterially induced crystal particle of another embodiment of the instant disclosure.

In some embodiments, the step S20 further comprises centrifuging the culture medium or applying other alternative means to isolate a precipitate from the culture medium. In some embodiments, after the precipitate is isolated from the culture medium, an oscillation procedure with high frequency, e.g., ultrasonication, is further applied to the precipitate to break the precipitate. In addition, in some embodiments, the precipitate may be washed by a solvent, and the washing may be one time or more than two times. Common solvents, e.g., water, ethanol, other alternative solvents, or any combination thereof, may be applied to wash the precipitate. For example, RO water, deionized water, or ethanol may be applied to wash the precipitate. Please refer to FIG. 5, in some embodiments, after the step S10, centrifuging the culture medium to form a precipitate (i.e., the wet powder material) (S200). And then, breaking the precipitate to form a crude powder material (S300), and washing the crude powder material by a solvent for at least once (S400). Last, air drying or heating the precipitate under a proper temperature to dry the precipitate (S500), so that the solvent in the precipitate is removed and the powder material is obtained. Furthermore, in some embodiments, the density of the powder material is 420 kg/m$^2$.

In some embodiments, the bacterially induced crystal particle may be utilized in preparing materials with great physical and/or chemical properties, e.g., in preparing a thermal conductive material. In some embodiments, the thermal conductive material may comprise the aforementioned bacterially induced crystal particle. In another embodiment, the thermal conductive material is formed by the aforementioned bacterially induced crystal particles. In some embodiments, the thermal conductivity of the bacterially induced crystal particles may be in a range of 0.027 to 0.15 Watt/meter*Kelvin (W/mK). In some embodiments, the thermal conductivity of the bacterially induced crystal particles may be 0.058 W/mK.

In some embodiments, the ingredients of the culture medium or the amount of the raw metal material may be adjusted to allow the composite shell of the bacterially induced crystal particle to be formed by two half portions in dome-shaped. For example, comparing with a normal culturing procedure, the saccharide (i.e., the carbon source) in the culture medium or the concentration of the raw metal material may be adjusted, so that the bacteria suffer a stress response and the shape of the bacteria are changed. In some embodiments, using the raw metal material in high concentration (e.g., 0.1 to 0.2 M), may facilitate the stress response to alter the shape of the bacteria in the culture medium. In some embodiments, the change in shape of the bacteria may cause the bacteria to form a structure having two dome-shaped portions, e.g., a sphere or a rod with two dome-shaped portions. Accordingly, the composite shell may have two half portions in dome-shaped. In some embodiments, the composite shell is spheric or rod-shaped with two half shells in dome-shaped.

In some embodiments, the composite shell of the bacterially induced crystal particle may further undergo an oxidation reaction, a sulfurization reaction, or a selenization reaction. For example, the metallic material may be reacted with oxygen in the environment to form an oxide of a transition metal under a high temperature (e.g., 300 to 1000 degree Celsius) and/or an oxygen-rich environment, and most of the composite shell is formed by the metallic material which is the transition metal oxide. Herein, the transition metal oxide is only formed by a transition metal element and oxygen atom(s), and excludes from transition metal carboxylate or compounds having oxygen atom(s). In another embodiment, for example, the composite shell treated by oxidation reaction may undergo a sulfurization by mechanical ablation or chemical vapor deposition, so that the oxygen atoms in the transition metal oxide of the metallic material can be replaced by sulfur atoms in the replacement reaction. In this embodiment, most of the composite shell is formed by the metallic material which is the transition metal sulfide. Similarly, the composite shell treated by oxidation reaction may undergo a selenization by mechanical ablation or chemical vapor deposition, so that the oxygen atoms in the transition metal oxide of the metallic material can be replaced by selenium atoms in the replacement reaction, and in this embodiment, most of the composite shell is formed by the metallic material which is the transition metal selenide. Furthermore, the changes of the characters of the composite shell before and after the oxidation, the sulfurization, and the selenization can be measured by Raman spectroscopy, photoluminescence spectroscopy, electron microscope, etc. For example, by utilizing photoluminescence spectroscopy to measure the composite shell, the energy gap of the metallic material of the composite shell is detected to be in a range of 1.2 to 1.8 eV (electron volt).

In some embodiments, the powder material may be placed in a reactor, and the powder material is heated with oxygen to oxidize, sulfur vapor (e.g., hydrogen sulfide) to sulfurize, or selenium vapor (e.g., hydrogen selenide) to selenize, under a temperature in a range of 300 to 1000 degree Celsius or under a proper temperature, for a period of time, so that the raw metal material further includes oxides of the transition metal, sulfides of the transition metal, or selenides of the transition metal. That is, the powered material is sintered. Accordingly, the composite shell of the bacterially induced crystal particle in the powder material undergoes an oxidation reaction, a sulfurization reaction, or a selenization reaction, so that most of the metallic material of the composite shell is a transition metal oxide, a transition metal sulfide, or a transition metal selenide. In some embodiments, after the composite shell undergoes the oxidation, the sulfurization, or the selenization, the weight percentage of biomaterial is in a range of 1 to 5% over the composite shell, and the weight percentage of the metallic material over the composite shell is greater than the weight percentage of the biomaterial over the composite shell.

For example, the bacterially induced crystal particle may be manufactured by following steps. Firstly, *Shewanella* sp. is obtained from white shrimp (scientific name: *Litopenaeus vannamei*). And then, under a 37 degree Celsius environment, the *Shewanella* sp. is cultured in a culture medium (e.g. an LB culture medium or a M9 culture medium) for 16 hours. Next, about 0.01 to 0.2 M carbon source and about 0.01 to 0.2 M tungstate are added into the culture medium, and the *Shewanella* sp. is further cultured for 3 to 5 days. After the culturing process, the culture medium is centrifuged to remove the supernatant and to obtain the precipitate. And then, the precipitate is ultrasonicated so as to break the precipitate. Next, the broken precipitate (i.e., the crude powder material) is washed by deionized water for several times, and the broken precipitate is suspended in ethanol. Last, the suspension is dried under 40 degree Celsius to obtain the powder material. The powder material comprises the bacterially induced crystal particle and is powder and inviscid.

The powder material is compressed to tablet powder material by a 10 MPa pressure for subsequent property measurements. Firstly, the volume and the weight of the tablet powder material are measured, and the density is calculated to be 420 kg/m$^2$. Under atmospheric environment, the tablet powder material is measured by a field emission scanning electron microscope (FESEM) (model: JEOL JSM-6500F) for SEM image analysis and energy-dispersive X-ray spectroscopy (EDS). In addition, the thermal conductive properties of the tablet powder material are analyzed by a Tci thermal conductivity analyzer with modified transition plane source (manufactured by C-Therm Technologies Ltd.). Furthermore, the main ingredients of the tablet powder material are analyzed by a Raman spectrometer.

Figure 6:
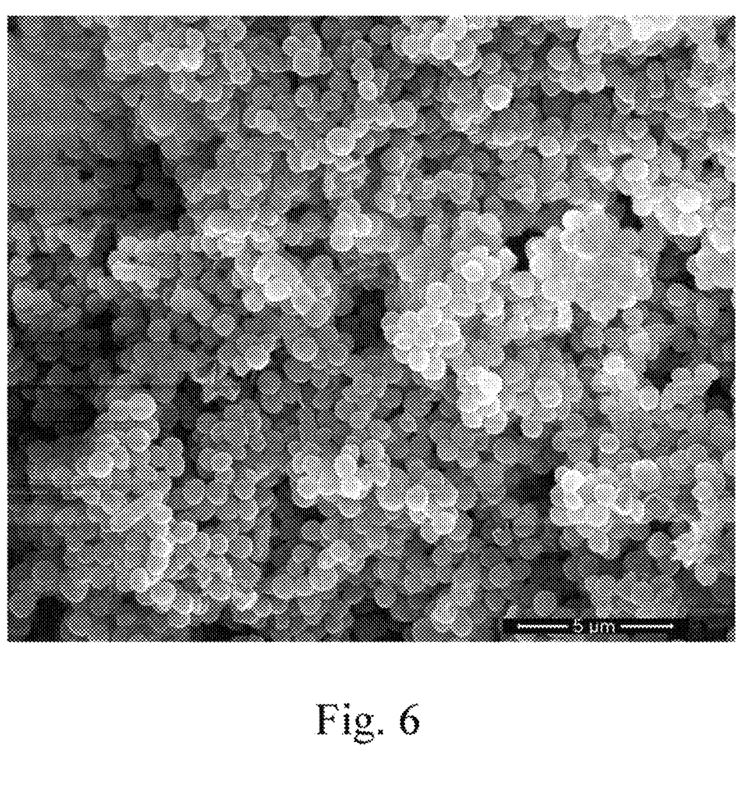
FIG. 6 illustrates a scanning electron microscope (SEM) graph of the bacterially induced crystal particle of one embodiment of the instant disclosure.

Please refer to FIG. 6. From the SEM image, bacterially induced crystal particles can be seen in the powder material. Each of the bacterially induced particles is spheric and has a smooth surface. The diameter of each of the bacterially induced particles is about 1 μm, and the thickness of each of the bacterially induced particles is about 20 to 40 nm. Therefore, air occupies the hollow space in the bacterially induced particles. In addition, the bacterially induced particles can bear such pressure and does not break or suffer any structural damages even if the powder material is compressed to form tablet powder material. From the analyzing result of the thermal conductivity properties of the tablet powder material, the thermal conductivity of the bacterially induced crystal particle is 0.058 W/mK, the thermal effusivity of the bacterially induced crystal particle is 124.22 WS$^{1/2}$/m$^2$K, and the thermal diffusivity of the bacterially induced crystal particle is 2.54 m$^2$/s. Because the hollow space in the bacterially induced particle is occupied by air, the thermal conductivity of the bacterially induced crystal particle is extremely low, only about two times of that of the stationary air.

Figure 7:
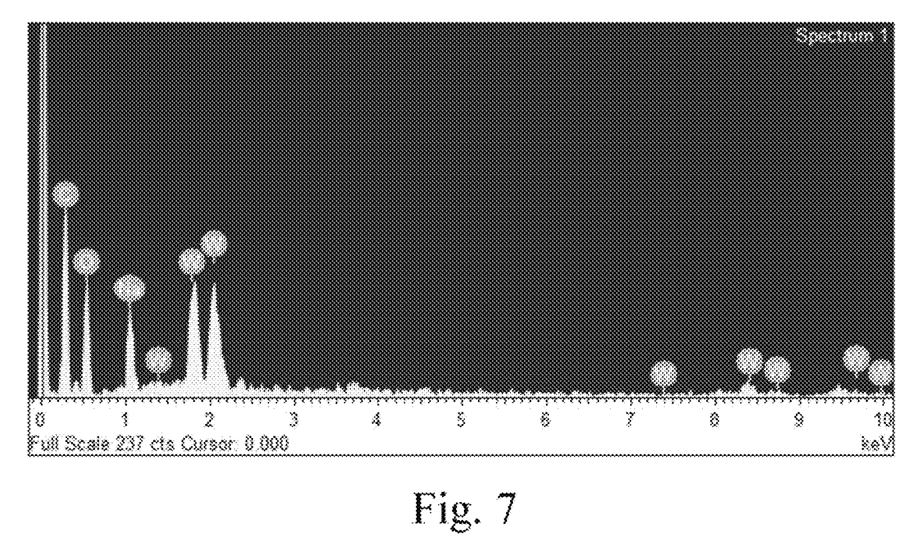
FIG. 7 illustrates an energy dispersive X-ray spectroscopy (EDS) graph of the bacterially induced crystal particle of one embodiment of the instant disclosure.
Figure 8:
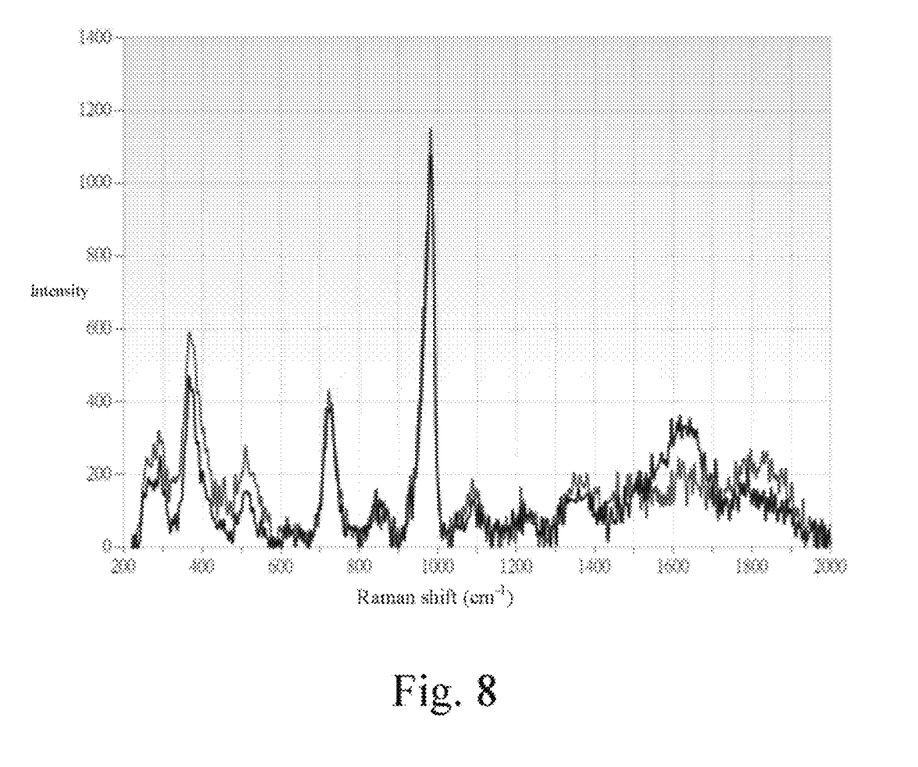
FIG. 8 illustrates a Raman spectroscopy graph of the bacterially induced crystal particle of one embodiment of the instant disclosure.

Please refer to FIG. 7. The EDS shows that elements comprising carbon, oxygen, tungsten, and other metals like sodium are detected in the composite shell of the bacterially induced crystal particle. As shown, the metallic material of the composite shell may comprise sodium tungstate. Furthermore, the crystalline, structure of tungsten oxides, like tungsten trioxide or tungsten dioxide is mainly in a three dimensional structure, while the crystalline structure of tungstate is mainly in a two dimensional structure. Therefore, the major ingredient of the metallic material may comprise sodium tungstate and other tungstate. Please refer to FIG. 8, the Raman spectroscopy shows that two major peaks are located at 980 cm$^{-1}$ and 737 cm$^{-1}$, respectively. The peak at 980 cm$^{-1}$ is mainly attributed by magnesium tungstate, and the peak at 737 cm$^{-1}$ is mainly attributed by sodium tungstate. Therefore, from FIGS. 7 and 8, the metal material mainly comprises magnesium tungstate and sodium tungstate.

According to embodiments of the instant disclosure, the thickness of the bacterially induced crystal particle is in nanometer scale, and the width is in micrometer scale. Therefore, it is inferred that the material occupancy ratio of the bacterially induced crystal particle is low. Next, as compared with the sodium tungstate having a density of 4179 kg/m$^3$, the density of the bacterially induced crystal particle is about 1/10 of that of sodium tungstate. Therefore, it is inferred that the volume ratio of the metallic material over the bacterially induced crystal particle is about 1/10. In general, when a material has low material occupancy ratio, the material also has a low thermal conductivity. In addition, when the bacterially induced crystal particle may be deemed as the combination of two dome structures, the shape of the bacterially induced crystal particle may be spheric or may be ellipsoid-shaped like rugby. In another embodiment, the bacterially induced crystal particle may be a rod having two dome-shaped portions. Because tungstate may be used as raw material of building stones, the bacterially induced crystal particle of the embodiments of the instant disclosure may be deemed as having a stone-made dome structure. For a stone-made dome structure, the thickness of the vault of the dome may be less than the thickness of the sidewall of the dome. In addition, the thickness of the vault may be greater than or equal to 1/73 of the diameter of the dome, and the thickness of the sidewall of the dome may be greater than or equal to 1/37 of the diameter of the dome, if the thickness of the sidewall of the dome is too thin, the dome would be fragile and the connection between the vault and the sidewall would break easily. Likewise, according to embodiments of the instant disclosure, in the case where the bacterially induced crystal particle is rod shaped, when the thickness of the cylindrical portion is less than 1/37 of the width of the bacterially induced particle, the connection between the cylindrical portion and the dome-shaped portions may be fragile and could break easily.

As above, the bacterially induced crystal particle, the thermal conductive material, and the method for manufacturing bacterially induced crystal particle, in accordance with one of the embodiments of the instant disclosure, are suitable for manufacturing a novel material. By utilizing principle of microorganism mineralization, bacterially induced crystal particle with low material occupation ratio and great thermal conductivity can be obtained. Moreover, the method for manufacturing the bacterially induced crystal particle is easy, low cost, and suitable for mass production. In addition, the structure of the bacterially induced crystal particle can be maintained upon compression by 10 MPa of pressure. Therefore, the bacterially induced crystal particle may be applied in mass production of a novel thermal conductive material, so that the thermal conductive material can have low thermal conductivity, great pressure resistance, and reduced manufacturing cost. Furthermore, the bacterially induced crystal particle, in accordance with one of the embodiments of the instant disclosure may be widely applied in developing products based on low thermal conductivity nanomaterial.

While the instant disclosure has been described by the way of example and in terms of the preferred embodiments, it is to be understood that the invention need not be limited to the disclosed embodiments. On the contrary, it is intended to cover various modifications and similar arrangements included within the spirit and scope of the appended claims, the scope of which should be accorded the broadest interpretation so as to encompass all such modifications and similar structures.

What is claimed is:

1. A method for manufacturing bacterially induced crystal particles, comprising:
   culturing bacteria in a culture medium comprising a carbon source and a raw metal material, so that the bacteria induce the raw metal material to undergo a reduction-oxidation reaction, wherein the raw metal material comprises a transition metal, and a concentration of the raw metal material is in a range of 0.1 to 0.2 M;
   isolating a wet powder material from the culture medium; and
   drying the wet powder material to obtain a powder material, wherein the powder material comprises at least one bacterially induced crystal particle;
      wherein in the step of culturing the bacteria in the culture medium, the bacteria suffers a stress response, so that a cell wall or a cell membrane of the bacteria forms a composite shell of the bacterially induced crystal particle,
      when the bacterially induced crystal particle is spheric, the composite shell is formed by two dome-shaped portions, and a thickness of each of the dome-shaped portions is not less than 1/73 of a diameter of the bacterially induced crystal particle, or
      when the bacterially induced crystal particle is rod-shaped, the composite shell is formed by a cylindrical portion and the two dome-shaped portions connected to two ends of the cylindrical portion, the thickness of each of the dome-shaped portions is not less than 1/73 of a width of the bacterially induced crystal particle, and a thickness of the cylindrical portion is not less than 1/37 of the width of the bacterially induced crystal particle.

2. The method for manufacturing bacterially induced crystal particle according to claim 1, wherein after the step of culturing the bacteria in the culture medium, further comprises:
   allowing an upper layer of the culture medium to form bubbles; and
   isolating a suspension from the bubbles to obtain the wet powder material.

3. The method for manufacturing bacterially induced crystal particle according to claim 1, wherein the bacteria is Gram-negative bacteria.

4. The method for manufacturing bacterially induced crystal particle according to claim 3, wherein the Gram-negative bacteria is *Shewanella* sp., *Pantoea* sp., *Pseudomonas aeruginosa, Bacillus subtilis*, or any combination thereof.

5. The method for manufacturing bacterially induced crystal particle according to claim 1, wherein the raw metal material includes an acid salt compound of the transition metal.

6. The method for manufacturing bacterially induced crystal particle according to claim 1, wherein the raw metal material is a salt compound of vanadic acid, niobic acid, tungstic acid, molybdenic acid, cobaltic acid, nickelic acid, zirconic acid, or any combination thereof.

7. The method for manufacturing bacterially induced crystal particle according to claim 1, wherein the bacteria is *Shewanella* sp., and the raw metal material is a salt compound of tungstic acid or molybdenic acid.

8. The method for manufacturing bacterially induced crystal particle according to claim 1, wherein the bacteria is *Pantoea* sp., and the raw metal material is a salt compound of molybdenic acid, tungstic acid, or vanadic acid.

9. The method for manufacturing bacterially induced crystal particle according to claim 1, wherein a density of the powder material is 420 kg/m$^3$.

10. The method for manufacturing bacterially induced crystal particle according to claim 1, wherein the step of culturing the bacteria in the culture medium comprises:
    culturing the bacteria in the culture medium under an oxygen atmosphere at 37 degree Celsius for a period of time.

11. The method for manufacturing bacterially induced crystal particle according to claim 1, wherein the culture medium is a LB medium or a M9 medium.

12. The method for manufacturing bacterially induced crystal particle according to claim 1, wherein a culture time in the step of culturing the bacteria in the culture medium is in a range of 3 to 5 days.

13. The method for manufacturing bacterially induced crystal particle according to claim 1, wherein a concentration of the carbon source in the culture medium is in a range of 0.01 to 0.2 M.

14. The method for manufacturing bacterially induced crystal particle according to claim 1, wherein the step of isolating the wet powder material from the culture medium comprises:
    centrifuging the culture medium to form a precipitate; and
    isolating the precipitate from the centrifuged culture medium to obtain the wet powder material.

15. The method for manufacturing bacterially induced crystal particle according to claim 14, wherein after the step of isolating the precipitate from the centrifuged culture medium, further comprises:
    breaking the wet powder material to form a crude powder material by ultrasonication.

16. The method for manufacturing bacterially induced crystal particle according to claim 15, wherein after the step of breaking the wet powder material, further comprises:
    washing the crude powder material by a solvent for at least once; and
    wherein the step of drying the wet powder material comprises:
    drying the crude powder material to obtain the powder material.

17. The method for manufacturing bacterially induced crystal particle according to claim 1, wherein the bacterially induced crystal particle is formed by a composite shell that encloses a hollow space, the composite shell comprises:
    a biomaterial, comprising a cell wall or a cell membrane of the bacteria; and
    a metallic material, comprising oxides, sulfides, selenides, acid salt compounds of a transition metal, or any combination thereof.

18. The method for manufacturing bacterially induced crystal particle according to claim 17, further comprising:
    heating the powder material in oxygen to oxidize the composite shell of the bacterially induced crystal particle, so that the raw metal material further comprises oxides of the transition metal.

19. The method for manufacturing bacterially induced crystal particle according to claim 17, further comprising:
    heating the powder material in a sulfur vapor to sulfurize the composite shell of the bacterially induced crystal particle, so that the raw metal material further comprises sulfides of the transition metal.

20. The method for manufacturing bacterially induced crystal particle according to claim 17, further comprising:
    heating the powder material in a selenium vapor to selenize the composite shell of the bacterially induced crystal particle, so that the raw metal material further comprises selenides of the transition metal.

* * * * *